United States Patent

Lunkenheimer et al.

Patent Number: 5,210,197
Date of Patent: May 11, 1993

[54] FUNGICIDAL SUBSTITUTED ANIMALS AND FUNGICIDAL USE THEREOF

[75] Inventors: Winfried Lunkenheimer, Wuppertal; Wilhelm Brandes, Leichlingen, both of Fed. Rep. of Germany

[73] Assignee: Bayer Aktiengesellschaft, Leverkusen, Fed. Rep. of Germany

[21] Appl. No.: 596,251

[22] Filed: Oct. 12, 1990

[30] Foreign Application Priority Data

Nov. 17, 1989 [DE] Fed. Rep. of Germany ....... 3938287

[51] Int. Cl.$^5$ ............... C07D 209/48; C07D 207/26; C07D 207/40; C07D 263/38; A61K 31/42; A61K 31/40
[52] U.S. Cl. .................. 548/231; 548/473; 548/543; 548/546
[58] Field of Search ............ 548/473, 231, 543, 546; 514/376, 417, 424, 425

[56] References Cited

FOREIGN PATENT DOCUMENTS 0294667 12/1988 European Pat. Off. .
9394758 3/1989 European Pat. Off. .
3719225 12/1988 Fed. Rep. of Germany .

Primary Examiner—David B. Springer
Attorney, Agent, or Firm—Sprung Horn Kramer & Woods

[57] ABSTRACT

Fungicidal substituted aminals of the formula

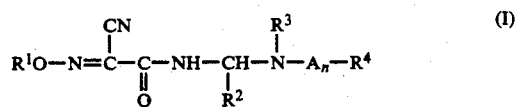

in which
A represents —CO—, —CS— or —SO$_2$—,
n represents 0 or 1,
R$^1$ represents optionally substituted alkyl, alkenyl, alkynyl, cycloalkyl or cycloalkenyl,
R$^2$ represents hydrogen or optionally substituted alkyl, alkenyl, alkynyl, cycloalkyl, cycloalkenyl, aryl or heterocyclyl,
R$^3$ represents optionally substituted alkyl or may represent in the case where either n is 1 and A represents —SO$_2$— or n is 1 and R$^4$ represents cycloalkoximino or arylthio,
R$^4$ represents hydrogen, optionally substituted alkyl, alkenyl or alkynyl or bridged or fused radicals, or 1-cyanoalkoximino, —OR$^5$, —SR$^5$ or —NR$^6$R$^7$, or
R$^3$ and R$^4$ together complete a ring.

6 Claims, No Drawings

FUNGICIDAL SUBSTITUTED ANIMALS AND FUNGICIDAL USE THEREOF

The present invention relates to new substituted aminals, several processors for their preparation and their use in agents for combating pests, in particular as fungicides.

It is already known that certain substituted 2-cyano-2-oximino-acetamides have a good fungicidal activity (compare, for example, European Patent 0,201,999, DE-OS (German Published Specification) 2,312,956 and DE-OS (German Published Specification) 3,602,243). However, the action of these compounds is not always completely satisfactory, especially when low amounts and concentrations are applied.

New substituted aminals of the general formula (I)

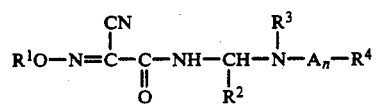

in which
A represents —CO—, —CS— or —SO$_2$—,
n represents 0 or 1,
R represents optionally substituted alkyl, substituents which may be mentioned being: halogen, cyano, —COOR$^I$, —CONR$^{II}$R$^{III}$, —OR$^{IV}$, acyl, optionally substituted aryl and in each case optionally substituted cycloalkyl and heterocyclyl; or
R$^1$ furthermore represents in each case optionally substituted alkenyl, alkynyl, cycloalkyl or cycloalkenyl,
R$^2$ represents hydrogen, or represents optionally substituted alkyl, substituents which may be mentioned being: cyano, alkoxy, alkylthio, —COOR$^I$, acylamino and in each case optionally substituted aryl, cycloalkyl and heterocyclyl; or
R$^2$ furthermore represents in each case optionally substituted alkenyl, alkynyl, cycloalkyl or cycloalkenyl, or represents in each case optionally substituted aryl or heterocyclyl,
R$^3$ represents optionally substituted alkyl, substituents which may be mentioned being: halogen, cyano, —COOR$^I$, —CONR$^{II}$R$^{III}$, —OR$^{IV}$, the oxo or thioxo group and in each case optionally substituted aryl, cycloalkyl and heterocyclyl; or furthermore represents in each case optionally substituted alkenyl, alkynyl, cycloalkyl or aryl, or represents optionally substituted and optionally fused heterocyclyl, or represents —OR$^V$; or furthermore
R$^3$ may represent hydrogen, in the case where either n is 1 and A represents —SO$_2$— or n is 1 and R$^4$ represents cycloalkoximino or arylthio,
R$^4$ represents hydrogen, or represents optionally substituted alkyl, substituents which may be mentioned being: halogen, alkoxy, alkylthio, alkylsulphinyl, alkylsulphonyl, acyloxy, acylamino, cyano, —COOR$^I$ and in each case optionally substituted aryl, cycloalkyl and heterocyclyl; or furthermore represents in each case optionally substituted alkenyl or alkynyl; or
R$^4$ furthermore represents in each case optionally bridged and/or fused and in each case optionally substituted cycloalkyl or cycloalkenyl, or represents in each case optionally fused and in each case optionally substituted aryl or heterocyclyl, or represents in each case optionally substituted aryloxy or arylthio, or represents alkoxycarbonyl, or represents 1-cyanoalkoximino, —OR$^5$, —SR$^5$ or —NR$^6$R$^7$, or
R$^3$ and R$^4$, together with the nitrogen atom and if appropriate the radical A, form an optionally substituted 4- to 9-membered saturated or unsaturated heterocyclic ring, which optionally contains further hetero atoms from the series comprising oxygen, sulphur and nitrogen and which is optionally fused by 1 or 2 saturated or unsaturated carbocyclic radicals,
R$^5$ represents hydrogen, or represents optionally substituted alkyl, substituents which may be mentioned being: halogen, —OR$^{IV}$, —SR$^{IV}$, —COOR$^I$, —CONR$^{II}$R$^{III}$, —CN, —NR$^{II}$R$^{III}$, acyl, in each case optionally substituted aryl and aryloxy and in each case optionally substituted cycloalkyl, cycloalkenyl and heterocyclyl; or furthermore represents in each case optionally substituted alkenyl or alkynyl, or represents in each case optionally substituted cycloalkyl or cycloalkenyl,
R$^6$ represents hydrogen, or represents optionally substituted alkyl, substituents which may be mentioned being: halogen, cyano, —COOR , —CONR$^{II}$R$^{III}$, —NR$^{II}$R$^{III}$, —OR$^{IV}$, —S(O)$_n$R$^{IV}$, acyl and in each case optionally substituted aryl, heterocyclyl, cycloalkyl and cycloalkenyl; or furthermore represents in each case optionally substituted alkenyl, alkynyl, cycloalkyl, cycloalkenyl, aryl or heterocyclyl, and
R$^7$ has the meaning of R$^6$ or represents —OR$^{IV}$, or
R$^6$ and R$^7$, together with the nitrogen atom to which they are bonded, represent an optionally substituted heterocyclic radical, which can contain further hetero atoms,
R$^1$ represents hydrogen or alkyl optionally substituted with the following substituents: halogen and in each case optionally substituted aryl, cycloalkyl and cycloalkenyl,
R$^{II}$ and R$^{III}$ are identical or different and represent hydrogen or alkyl optionally substituted with the following substituents: halogen, —COOR$^{IV}$, —CONR$^I$R$^{IV}$ and in each case optionally substituted aryl, aralkyl, cycloalkyl and cycloalkenyl; or R$^{II}$ and R$^{III}$ furthermore represent alkenyl, alkinyl or in each case optionally substituted cycloalkyl, cycloalkenyl, aryl or heterocyclyl, or together with the nitrogen atom to which they are bonded represent an optionally substituted heterocyclic radical, which can contain further hetero atoms,
R$^{IV}$ represents hydrogen, alkyl, aralkyl or acyl and
R$^V$ represents hydrogen, alkyl or aralkyl, have now been found.

The compounds of the formula (I) can occur in the form of various geometric isomers, depending on the arrangement of the substituents on the C=N grouping (E- or Z-isomer). Both the pure Z- and E-isomers and mixtures thereof are claimed according to the invention.

Where appropriate, the compounds have one or more asymmetric carbon atoms; they can thus also be in the form of enantiomers or diastereomers, which can be obtained in various proportions. They are predominantly obtained as racemates. Both the pure enantiomers and diastereomers and the mixtures are claimed according to the invention.

For simplicity, compounds of the formula (I) are always referred to below, although both the pure compounds and the mixtures with various contents of isomeric, enantiomeric and diastereomeric compounds are meant.

It has furthermore been found that the new substituted aminals of the general formula (I)

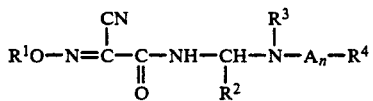
(I)

in which A, n, $R^1$, $R^2$, $R^3$ and $R^4$ have the abovementioned meanings, are obtained by a process in which
a) 2-cyano-2-oximinocarbonyl compounds of the formula (II)

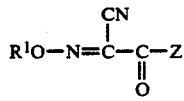
(II)

in which
$R^1$ has the abovementioned meaning and
Z represents chlorine, methoxy or ethoxy, are reacted with amino compounds of the formula (III)

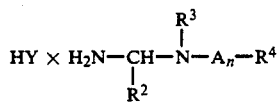
(III)

in which $R^2$, $R^3$, $R^4$, A and n have the abovementioned meanings and HY represents the equivalent of an inorganic or organic acid, if appropriate in the presence of a base and in the presence of a diluent and if appropriate in the presence of a catalyst; or
b) 2-cyano-2-oximinoacetamides of the formula (IV)

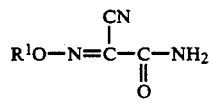
(IV)

in which $R^1$ has the abovementioned meaning, are reacted with compounds of the formula (V)

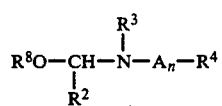
(V)

in which
$R^2$, $R^3$, $R^4$, A and n have the abovementioned meanings and
$R^8$ represents hydrogen, methyl or acetyl, if appropriate in the presence of an acid and if appropriate in the presence of a diluent; or
c) 2-cyano-2-oximinoacetamides of the formula (IV)

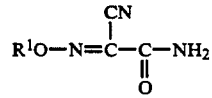
(IV)

in which $R^1$ has the abovementioned meaning, are reacted with halogen compounds of the formula (VI)

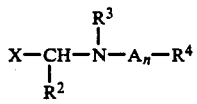
(VI)

in which
$R^2$, $R^3$, $R^4$, A and n have the abovementioned meanings and
X represents chlorine or bromine, if appropriate in the presence of a base and if appropriate in the presence of a diluent.
The compounds of the formula (Ia) according to the invention

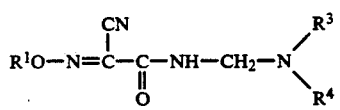
(Ia)

in which $R^1$, $R^3$ and $R^4$ have the abovementioned meanings, are obtained by a process in which
d) 2-cyano-2-oximinoacetamides of the formula (IV)

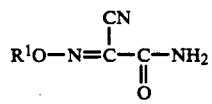
(IV)

in which $R^1$ has the abovementioned meaning, are reacted with amines of the formula (VII)

(VII)

in which $R^3$ and $R^4$ have the abovementioned meanings, and with formaldehyde, if appropriate in the presence of a diluent.
The compounds of the formula (Ib) according to the invention

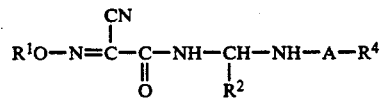
(Ib)

in which $R^1$, $R^2$, $R^4$ and A have the abovementioned meanings, are obtained by a process in which
e) N-(2-cyano-2-oximino-acetyl)-aminals of the formula (VIII)

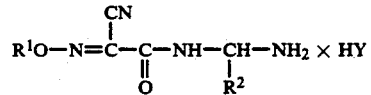
(VIII)

in which $R^1$ and $R^2$ have the abovementioned meanings and HY represents the equivalent of an inorganic or organic acid, are reacted with an acylating reagent of the formula (IX)

$Q-A-R^4$     (IX)

in which
$R^4$ and A have the abovementioned meanings and

Q represents a customary leaving group, such as halogen, alkoxy, alkylthio, —O—COR$^4$, —O—COOR$^5$, —OR$^5$, —SR$^5$, carboxymethoxy or carboxymethylthio, if appropriate in the presence of a base and in the presence of a diluent, and if appropriate in the presence of a catalyst.

Finally, it has been found that the new substituted aminals have, inter alia, potent fungicidal properties. Surprisingly, the compounds according to the invention exhibit a more potent action in this respect than the substituted 2-cyano-2-oximinoacetamides known from the prior art, which are closely related compounds structurally and from the point of view of their action. The substances according to the invention thus represent an enrichment of the art.

In the following, all the aliphatic radicals, such as alkyl, alkoxy, alkenyl and the like, by themselves or in combinations, such as alkoxyalkyl, can be straight-chain or branched, and the aliphatic radicals can furthermore in general preferably be substituted by one to five, particularly preferably one to three or especially preferably one or two identical or different substituents; all the ring systems are likewise optionally substituted by one to five, particularly preferably one to three or especially preferably one or two, identical or different substituents, unless stated otherwise or expressly described.

Formula (I) provides a general definition of the substituted aminals according to the invention. Preferably, in this formula (I), A represents —CO—, —CS— or —SO$_2$—, n represents 0 or 1, R$^1$ represents straight-chain or branched alkyl having 1 to 6 carbon atoms which is optionally substituted by one to five identical or different substituents, possible substituents being the following: fluorine, chlorine, bromine, iodine, cyano, —COOR$^I$, —CONR$^{II}$R$^{III}$, —OR$^{IV}$, acyl having 2 to 9 carbon atoms and phenyl which is optionally substituted by one to five identical or different substituents, substituents on the phenyl which may be mentioned being: halogen, alkyl and alkoxy having in each case 1 to 4 carbon atoms and halogenoalkyl and halogenoalkoxy having in each case 1 or 2 carbon atoms and 1 to 5 identical or different halogen atoms; further substituents on the alkyl are cycloalkyl having 3 to 6 carbon atoms which is optionally substituted by one to five identical or different alkyl radicals having 1 to 4 carbon atoms, and 3- to 6-membered heterocyclyl having 1 to 3 identical or different hetero atoms, such as nitrogen, oxygen and sulphur atoms, which is optionally substituted by one to five identical or different halogen atoms and alkyl groups having 1 to 4 carbon atoms and is optionally fused by 1 or 2 6-membered saturated or unsaturated carbocyclic radicals; R$^1$ furthermore preferably represents straight-chain or branched alkenyl or alkynyl having 2 to 6 carbon atoms, in each case optionally substituted by one to three identical or different alkyl groups having 1 to 4 carbon atoms; R$^1$ moreover preferably represents cycloalkyl having 3 to 6 carbon atoms or cycloalkenyl having 5 to 7 carbon atoms, in each case optionally substituted by one to five identical or different alkyl groups having 1 to 4 carbon atoms;

R$^2$ represents hydrogen, or represents straight-chain or branched alkyl having 1 to 6 carbon atoms which is optionally substituted by one to five identical or different substituents, the following substituents being possible: cyano, alkoxy and alkylthio having in each case 1 to 4 carbon atoms, —COOR$^I$, acylamino having 2 to 9 carbon atoms and phenyl which is optionally substituted by one to five identical or different substituents, possible substituents being the substituents on phenyl already mentioned as preferred for R$^1$; further alkyl substituents are cycloalkyl having 3 to 6 carbon atoms which is optionally substituted by one to five identical or different alkyl groups having 1 to 4 carbon atoms, and 3- to 6-membered heterocyclyl having 1 to 3 identical or different hetero atoms, such as nitrogen, oxygen and sulphur atoms, which is optionally substituted by one to five identical or different halogen atoms and alkyl groups having 1 to 4 carbon atoms and is optionally fused by 1 or 2 6-membered saturated or unsaturated carbocyclic radicals; R$^2$ furthermore preferably represents straight-chain or branched alkenyl or alkynyl having 2 to 6 carbon atoms, in each case optionally substituted by one to three identical or different substituents, substituents which may be mentioned being: phenyl which is optionally substituted by one to five identical or different halogen atoms and alkyl groups having 1 to 4 carbon atoms; R$^2$ moreover preferably represents cycloalkyl having 3 to 6 carbon atoms or cycloalkenyl having 5 to 7 carbon atoms, in each case optionally substituted by one to five identical or different alkyl groups having 1 to 4 carbon atoms; R$^2$ furthermore preferably represents phenyl which is optionally substituted by one to five identical or different substituents, possible substituents being the substituents on phenyl already mentioned as preferred for R$^1$; R$^2$ furthermore preferably represents 3- to 6-membered heterocyclyl having 1 to 3 identical or different hetero atoms, such as nitrogen, oxygen and sulphur atoms, which is optionally substituted by one to five identical or different halogen atoms and alkyl groups having 1 to 4 carbon atoms and is optionally fused by 1 or 2 6-membered saturated or unsaturated carbocyclic radicals;

R$^3$ represents straight-chain or branched alkyl having 1 to 6 carbon atoms which is optionally substituted by one to five identical or different substituents, the following substituents being possible: fluorine, chlorine, bromine, iodine, cyano, —COOR$^I$, —CONR$^{II}$R$^{III}$, —OR$^{IV}$, the oxo or thioxo group and phenyl which is optionally substituted by one to five identical or different substituents, possible substituents being the substituents on phenyl already mentioned as preferred for R$^1$; further substituents on alkyl are cycloalkyl having 3 to 6 carbon atoms which is optionally substituted by one to five identical or different alkyl groups having 1 to 4 carbon atoms, and 3- to 6-membered heterocyclyl having 1 to 3 identical or different hetero atoms, such as nitrogen, oxygen and sulphur atoms, which is optionally substituted by one to five identical or different substituents from the group comprising halogen, alkyl, alkoxy and alkylthio having in each case 1 to 4 carbon atoms, hydroxyl, the oxo or thioxo group, carboxyl, alkoxycarbonyl having 1 to 4 carbon atoms in the alkoxy part and carbamoyl; R$^3$ furthermore preferably represents straight-chain or branched alkenyl or alkynyl having in each case 2 to 6 carbon atoms and in each case optionally substituted by one to three identical or different halogen atoms or alkyl groups having 1 to 4 carbon atoms; R$^3$ moreover preferably represents cycloalkyl having 3 to 6 carbon atoms, in each case optionally substituted by one to five identical or different alkyl groups having 1 to 4 carbon atoms; or represents phenyl which is optionally substituted by one to five identical or different substituents, possible substituents being the substituents on phenyl already mentioned as preferred for R¹; R³ furthermore preferably represents 3- to 6-membered heterocyclyl having 1 to 3 identical or different hetero atoms, such as nitrogen, oxygen and sulphur atoms, which is optionally substituted by one to five identical or different substituents from the group comprising halogen, alkyl, alkoxy and alkylthio having in each case 1 to 4 carbon atoms, hydroxyl, mercapto, the oxo or thioxo group, carboxyl, alkoxycarbonyl having 1 to 4 carbon atoms in the alkoxy part and carbamoyl; 1 or 2 6-membered saturated or unsaturated carbocyclic radicals are optionally fused to the heterocyclyl radical, or furthermore represents —OR$^V$; and in addition R³ may represent hydrogen, in the case where either n is 1 and A represents —SO₂— or n is 1 and R⁴ represents cyanoalkoximino or arylthio, R⁴ represents hydrogen or represents straight-chain or branched alkyl having 1 to 6 carbon atoms which is optionally substituted by one to five identical or different substituents, the following substituents being possible: fluorine, chlorine, bromine, iodine, cyano, alkoxy, alkylthio, alkylsulphinyl and alkylsulphonyl having in each case 1 to 4 carbon atoms, acyloxy and acylamino having in each case 2 to 9 carbon atoms, —COOR$^I$ and phenyl which is optionally substituted by one to five identical or different substituents, possible substituents being the substituents on phenyl already mentioned as preferred for R¹; further substituents on alkyl are cycloalkyl having 3 to 6 carbon atoms which is optionally substituted by one to five identical or different alkyl groups having 1 to 4 carbon atoms, and 3- to 6-membered heterocyclyl having 1 to 3 identical or different hetero atoms, such as nitrogen, oxygen and sulphur atoms, which is optionally substituted by one to five identical or different halogen atoms and alkyl groups having 1 to 4 carbon atoms and is optionally substituted by 1 or 6-membered saturated or unsaturated carbocyclic radicals; R⁴ furthermore preferably represents straight-chain or branched alkenyl or alkynyl having in each case 2 to 6 carbon atoms and in each case optionally substituted by one to three identical or different substituents, substituents which may be mentioned being: alkyl having 1 to 4 carbon atoms and phenyl which is optionally substituted by one to five identical or different halogen atoms and alkyl groups having 1 to 4 carbon atoms; R⁴ furthermore preferably represents cycloalkyl having 3 to 6 carbon atoms or cycloalkenyl having 5 to 7 carbon atoms, in each case optionally bridged with methylene or ethylene and/or fused with 1 or 2 benzene, cyclopentane or cyclohexane rings and in each case optionally substituted by one to five identical or different substituents, substituents which may be mentioned being: halogen, alkyl and alkoxy having in each case 1 to 4 carbon atoms, acyloxy and acylamino having in each case 2 to 5 carbon atoms, the oxo group, phenyl, hydroxycarbonyl and alkoxycarbonyl having 1 to 4 carbon atoms in the alkoxy part; R⁴ moreover preferably represents phenyl which is optionally fused with 1 or 2 benzene or cyclohexane rings and is optionally substituted by one to five identical or different substituents, substituents which may be mentioned being: halogen, hydroxyl, nitro, alkyl and alkoxy having in each case 1 to 4 carbon atoms, halogenoalkyl and halogenoalkoxy having in each case 1 or 2 carbon atoms and 2 to 5 identical or different halogen atoms, such as fluorine and chlorine atoms, acylamino and acylalkylamino having in each case 2 to 5 carbon atoms in the acyl part and 1 to 4 carbon atoms in the alkyl part, carboxyl and alkoxycarbonyl having 1 to 4 carbon atoms in the alkoxy part; R⁴ furthermore represents phenoxy or phenylthio, in each case optionally substituted by one to five identical or different substituents, possible substituents being the abovementioned substituents on phenyl; R⁴ furthermore preferably represents 5-or 6-membered heterocyclyl having 1 to 3 identical or different hetero atoms, such as nitrogen, oxygen and sulphur atoms, which is optionally fused with 1 or 2 benzene or cyclohexane rings and is optionally substituted by one to five identical or different substituents, substituents which may be mentioned being: halogen, alkyl having 1 to 4 carbon atoms, acyl having 2 to 9 carbon atoms, phenyl, the oxo group and hydroxyl; R⁴ finally also preferably represents alkoxycarbonyl having 1 to 4 carbon atoms in the alkoxy part, or represents 1-cyanoalkoximino having 1 or 2 carbon atoms in the alkoxy part, or represents —OR⁵, —SR⁵ or —NR⁶R⁷; or R³ and R⁴, together with the nitrogen atom and if appropriate the radical A, form a 5- to 7-membered saturated or unsaturated heterocyclic ring which optionally contains a further 1 or 2 identical or different hetero atoms from the series comprising oxygen, sulphur and nitrogen, is optionally substituted by one to five identical or different substituents and is optionally fused by 1 or 2 6-membered saturated or unsaturated carbocyclic radicals, substituents which may be mentioned being: halogen, alkyl, alkylthio and alkoxy having in each case 1 to 4 carbon atoms, hydroxyl, mercapto, the oxo or thioxo group, carboxyl, alkoxycarbonyl having 1 to 4 carbon atoms in the alkoxy part, carbamoyl, (di)alkylcarbamoyl having 1 to 4 carbon atoms in the particular alkyl parts, phenyl which is optionally substituted by one to five identical or different substituents, possible substituents being halogen and alkyl having 1 to 4 carbon atoms, and 5- or 6-membered heterocyclyl having 1 to 3 identical or different hetero atoms from the series comprising oxygen, sulphur and nitrogen, which is optionally substituted by one to five identical or different substituents, possible substituents being halogen and alkyl having 1 to 4 carbon atoms;

R⁵ represents hydrogen, or represents straight-chain or branched alkyl having 1 to 6 carbon atoms which is optionally substituted by one to five identical or different substituents, the following substituents being possible: halogen, —OR$^{IV}$, —SR$^{IV}$, —COOR$^I$, —CONR$^{II}$R$^{III}$, CN —NR$^{II}$R$^{III}$, acyl having 2 to 9 carbon atoms, phenyl and phenoxy, in each case optionally substituted by one to five identical or different halogen atoms and alkyl groups having 1 to 4 carbon atoms, cycloalkyl having 3 to 6 carbon atoms and cycloalkenyl having 5 to 7 carbon atoms, in each case optionally substituted by one to five identical or different alkyl groups having 1 to 4 carbon atoms, and 3- to 6-membered heterocyclyl having 1 to 3 identical or different hetero atoms, such as nitrogen, oxygen and sulphur atoms, which is optionally substituted by one to five identical or different halogen atoms and alkyl groups having 1 to 4 carbon atoms; R⁵ furthermore preferably represents alkenyl or alkynyl having in each case 2 to 6 carbon atoms and in each case optionally substituted by one to five identical or different alkyl groups having 1 to 4 carbon atoms, or represents cycloalkyl having 3 to 6 carbon atoms and cycloalkenyl having 5 to 7 carbon atoms, in each case optionally substituted by one to five identical or different alkyl groups having 1 to 4 carbon atoms;

R[6] represents hydrogen, or represents straight-chain or branched alkyl having 1 to 4 carbon atoms which is optionally substituted by one or two identical or different substituents, preferred substituents which may be mentioned being: halogen, cyano, —COOR[I], —CONR[II]R[III], —NR[II]R[III], —OR[IV], —S(O)$_n$R[IV], acyl having 2 to 9 carbon atoms, phenyl which is optionally substituted by one to five identical or different halogen atoms and alkyl groups having 1 to 4 carbon atoms, 5- or 6-membered heterocyclyl having 1 to 3 identical or different hetero atoms, for example nitrogen, oxygen and sulphur, which is optionally substituted by one to five identical or different halogen atoms and alkyl and alkoxy groups having in each case 1 to 4 carbon atoms, and cycloalkyl having 3 to 6 carbon atoms and cycloalkenyl having 5 to 7 carbon atoms, in each case optionally substituted by one to five identical or different alkyl groups having 1 to 4 carbon atoms; R[6] furthermore preferably represents straight-chain or branched alkenyl or alkynyl having in each case 2 to 6 carbon atoms; or represents cycloalkenyl having 5 to 7 carbon atoms which is optionally substituted by one to five identical or different alkyl groups having 1 to 4 carbon atoms, or represents cyloalkyl having 3 to 6 carbon atoms which is optionally substituted by one to five identical or different substituents, preferred substituents which may be mentioned being: halogen, alkyl and alkoxy having in each case 1 to 4 carbon atoms, cyano, amino, carbamoyl, alkylamino, dialkylamino, alkylcarbamoyl and dialkylcarbamoyl having in each case 1 to 4 carbon atoms in each alkyl part, alkoxycarbonylamino having 1 to 4 carbon atoms in the alkoxy part, cycloalkyl and cycloalkylalkyl having 5 or 6 carbon atoms in the cycloalkyl part and 1 to 4 carbon atoms in the straight-chain or branched alkyl part, phenyl which is optionally substituted by one to five identical or different halogen atoms and alkyl groups having 1 to 4 carbon atoms and pyrrolidone; R[6] furthermore preferably represents phenyl which is optionally substituted by one to five identical or different substituents from the group comprising halogen, alkyl and alkoxy having in each case 1 to 4 carbon atoms and halogenoalkyl and halogenoalkoxy having in each case 1 or 2 carbon atoms and 1 to 5 identical or different halogen atoms, or represents a 5- or 6-membered heterocyclic radical having 1 to 3 identical or different hetero atoms, such as, in particular, nitrogen, oxygen and sulphur atoms, which is optionally substituted by one to five identical or different substituents; substituents which may be mentioned are: halogen, mercapto, phenyl and straight-chain or branched alkyl, alkoxy, alkylthio, alkylsulphinyl and alkylsulphonyl having 1 to 4 carbon atoms per alkyl part;

R[7] has the meanings of R[6] or represents the grouping —OR[IV]; or

R[6] and R[7], together with the nitrogen atom to which they are bonded, represent a mono-, bi- or tricyclic heterocyclic or spiroheterocyclic radical having one to three further identical or different hetero atoms, such as oxygen, nitrogen or sulphur atoms, which is optionally substituted by one to five identical or different substituents, substituents which may be mentioned being: straight-chain or branched alkyl or alkoxy having in each case 1 to 4 carbon atoms, cycloalkyl having 3 to 6 carbon atoms, the hydroxyl or the oxo group, straight-chain or branched alkenyl having 2 to 4 carbon atoms, carboxyl, alkoxycarbonyl having 1 to 4 carbon atoms in the straight-chain or branched alkyl part, carbamoyl, alkyl- and dialkylcarbamoyl having in each case 1 to 4 carbon atoms in each straight-chain or branched alkyl part, and phenyl and phenylalkyl having 1 to 4 carbon atoms in the straight-chain or branched alkyl part, in each case optionally substituted by one or two identical or different substituents from the group comprising halogen and straight-chain or branched alkyl and alkoxy having in each case 1 to 4 carbon atoms;

R[I] represents hydrogen or straight-chain or branched alkyl having 1 to 6 carbon atoms, R[II] and R[III] are identical or different and represent hydrogen, straight-chain or branched alkyl having 1 to 6 carbon atoms and phenylalkyl which has 1 to 4 carbon atoms in the straight-chain or branched alkyl part and is optionally substituted by one to five identical or different substituents, substituents on phenyl which may be mentioned being: halogen, alkyl and alkoxy having in each case 1 to 4 carbon atoms, and halogenoalkyl and halogenoalkoxy having in each case 1 or 2 carbon atoms and 2 to 5 identical or different halogen atoms; R[II] furthermore represents alkoxycarbonylalkyl, carbamoylalkyl, alkylcarbamoylalkyl or dialkylcarbamoylalkyl having in each case 1 to 4 carbon atoms in each alkyl part, or represents cycloalkyl having 3 to 6 carbon atoms which is optionally substituted by one to five identical or different straight-chain or branched alkyl radicals having 1 to 4 carbon atoms;

R[IV] represents hydrogen, straight-chain or branched alkyl having 1 to 6 carbon atoms or phenylalkyl which has 1 to 4 carbon atoms in the straight-chain or branched alkyl part and is optionally substituted by one to five identical or different substituents, preferred possible substituents on phenyl being the substituents on phenyl mentioned for R[II]; R[IV] furthermore represents acyl having 2 to 9 carbon atoms; and R[V] represents hydrogen, straight-chain or branched alkyl having 1 to 6 carbon atoms or phenylalkyl which has 1 to 4 carbon atoms in the straight-chain or branched alkyl part and is optionally substituted by one to five identical or different substituents, possible substituents on phenyl being the substituents on phenyl mentioned for R[II].

Particularly preferred substituted aminals of the general formula (I) are those in which A represents —CO—, —CS— or —SO$_2$—, n represents 0 or 1, R[1] represents straight-chain or branched alkyl having 1 to 4 carbon atoms which is optionally substituted by one to three identical or different substituents, the following substituents being possible: fluorine, chlorine, bromine, iodine, cyano, —COOR[I], —CONR[II]R[III], —OR[IV], acyl having 2 to 9 carbon atoms, phenyl which is optionally substituted by one to three identical or different substituents from the group comprising fluorine, chlorine, methyl and methoxy, cyclopropyl or cyclohexyl, in each case optionally substituted by one to three methyl groups, and heterocyclic radicals of the formulae

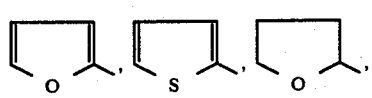

-continued

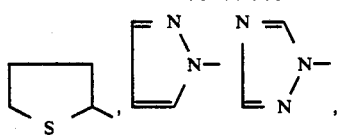

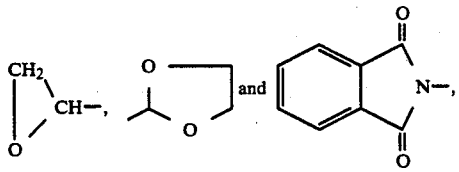

which are optionally substituted by one to three identical or different alkyl groups having 1 or 2 carbon atoms;

$R^1$ furthermore represents allyl or propargyl which is optionally substituted by one or two methyl groups, or represents cyclopropyl, cyclohexyl, cyclopentenyl or cyclohexenyl, in each case optionally substituted by one to three methyl groups;

$R^2$ represents hydrogen, or represents straight-chain or branched alkyl having 1 to 4 carbon atoms which is optionally substituted by one to three identical or different substituents, the following substituents being possible: cyano, methoxy, ethoxy, methylthio, ethylthio, —COOR$^I$, acylamino having 2 to 9 carbon atoms, phenyl which is optionally substituted by one to three identical or different substituents from the group comprising halogen, methyl and methoxy, cyclopropyl and cyclohexyl, in each case optionally substituted by one to three methyl groups, and heterocyclic radicals of the formulae

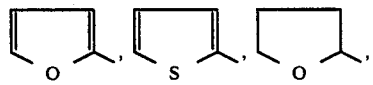

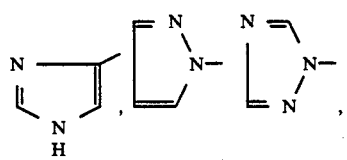

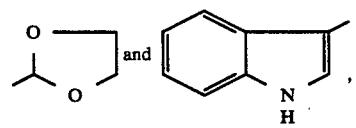

optionally substituted by one to three identical or different alkyl groups having 1 or 2 carbon atoms;

$R^2$ furthermore represents allyl, allenyl, vinyl, propargyl or ethynyl, in each case optionally substituted by phenyl, which can be optionally substituted by one to three identical or different substituents from the group comprising halogen and methyl; $R^2$ moreover represents cyclopropyl, cyclohexyl, cyclopentenyl or cyclohexenyl; $R^2$ furthermore represents phenyl which is optionally substituted by one to three identical or different substituents from the group comprising halogen, methyl and methoxy, or represents heterocyclic radicals of the formulae

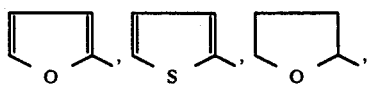

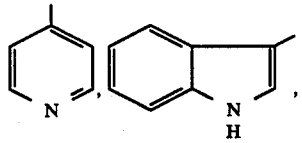

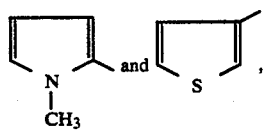

optionally substituted by one to three identical or different alkyl groups having 1 or 2 carbon atoms;

$R^3$ represents straight-chain or branched alkyl having 1 to 4 carbon atoms which is optionally substituted by one to three identical or different substituents, the following substituents being possible: fluorine, chlorine, bromine, iodine, cyano, —COOR$^I$, —CONR$^{II}$R$^{III}$, —OR$^{IV}$, the oxo or thioxo group and phenyl which is optionally substituted by one to three identical or different substituents from the group comprising fluorine, chlorine, methyl and methoxy; further substituents on alkyl are cyclopropyl, cyclopentyl and cyclohexyl, in each case optionally substituted by one to three identical or different substituents from the group comprising halogen and methyl, and heterocyclyl of the formulae:

optionally substituted by one to three identical or different substituents from the group comprising chlorine, methyl, methoxy, hydroxyl, methylthio, the oxo or thioxo group, carboxyl, methoxycarbonyl, ethoxycarbonyl and carbamoyl;

$R^3$ furthermore represents allyl or propargyl which is optionally substituted by one or two substituents from the group comprising halogen and methyl; or represents cyclopropyl, cyclopentyl or cyclohexyl, in each case optionally substituted by one to three methyl groups; or represents phenyl which is optionally substituted by one to three identical or different substituents from the group comprising fluorine, chlorine, methyl and methoxy; or represents a heterocyclic radical of the formula

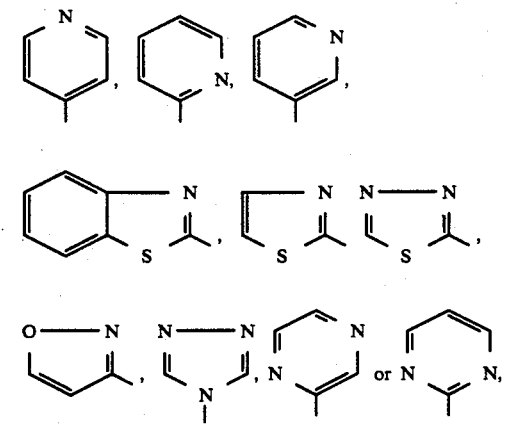

which is optionally substituted by one to three identical or different substituents from the group comprising fluorine, chlorine, methyl, methoxy, methylthio, hydroxyl, mercapto, the oxo or thioxo group, carboxyl, methoxycarbonyl, ethoxycarbonyl and carbamoyl, or furthermore represents $OR^V$; and furthermore $R^3$ may represent hydrogen in the case where either n is 1 and A represents $-SO_2-$ or n is 1 and $R^4$ represents cyanomethoximino or phenylthio, $R^4$ represents hydrogen, or represents straight-chain or branched alkyl having 1 to 4 carbon atoms which is optionally substituted by one to three identical or different substituents, the following substituents being possible: fluorine, chlorine, bromine, iodine, cyano, alkoxy, alkylthio, alkylsulphinyl and alkylsulphonyl having in each case 1 or 2 carbon atoms, acyloxy and acylamino having in each case 2 to 9 carbon atoms, $-COOR^I$, phenyl, cyclopropyl, cyclopentyl and cyclohexyl, optionally substituted by one to three identical or different substituents from the group comprising halogen and methyl, and heterocyclic radicals of the formulae

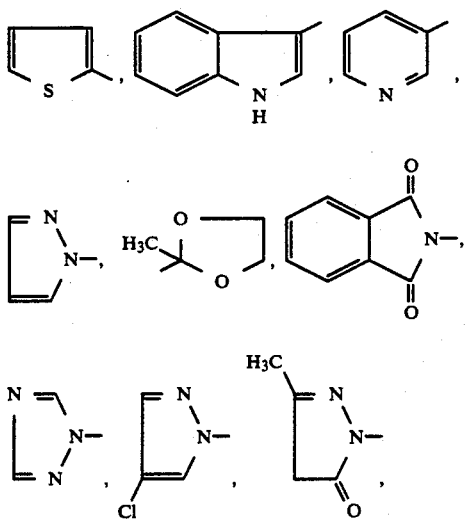

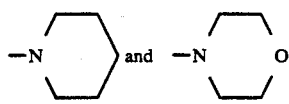

optionally substituted by one to three identical or different alkyl groups having 1 or 2 carbon atoms; $R^4$ furthermore represents vinyl, allyl or ethynyl, in each case optionally substituted by methyl or phenyl, which can be optionally substituted by one to three identical or different substituents from the group comprising halogen and methyl; $R^4$ furthermore represents cyclopropyl, cyclopentyl, cyclohexyl, cyclopentenyl or cyclohexenyl, in each case optionally bridged with methylene or ethylene and/or fused with 1 or 2 benzene, cyclopentane or cyclohexane rings and in each case optionally substituted by one to three identical or different substituents, substituents which may be mentioned being: halogen, methyl, methoxy, acyloxy and acylamino having in each case 2 to 5 carbon atoms, the oxo group, phenyl, hydroxycarbonyl and methoxy- and ethoxycarbonyl; $R^4$ moreover represents phenyl which is optionally fused with 1 or 2 benzene or cyclohexane rings and is optionally substituted by one to three identical or different substituents, substituents which may be mentioned being: fluorine, chlorine, hydroxyl, nitro, methyl, methoxy, acylamino and N-alkyl-acyl-amino having in each case 2 to 5 carbon atoms in the acyl part and 1 or 2 carbon atoms in the alkyl part, carboxyl and methoxy- and ethoxycarbonyl; $R^4$ represents phenoxy or phenylthio, in each case optionally substituted by one to three identical or different substituents, possible substituents being the abovementioned substituents on phenyl; $R^4$ furthermore represents 5- or 6-membered heterocyclyl having 1 to 3 identical or different hetero atoms, such as nitrogen, oxygen and sulphur atoms, which is optionally fused with 1 or 2 benzene or cyclohexane rings and optionally substituted by one to three identical or different substituents, substituents which may be mentioned being: acyl having 2 to 5 carbon atoms, chlorine, bromine, methyl, ethyl, phenyl, oxo and hydroxyl; $R^4$ finally also represents alkoxycarbonyl having 1 or 2 carbon atoms in the alkoxy part, or represents 1-cyanomethoximino, $-OR^5$, $-SR^5$ or $-NR^6R^7$; or $R^3$ and $R^4$ together represent a heterocyclyl of the formula

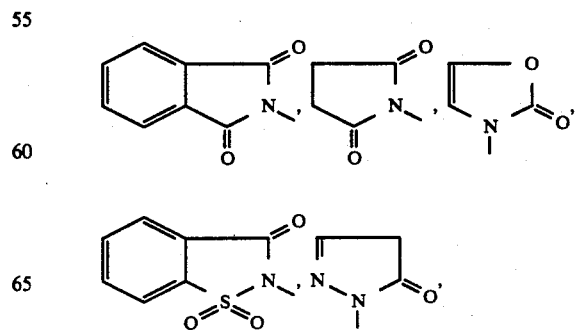

-continued

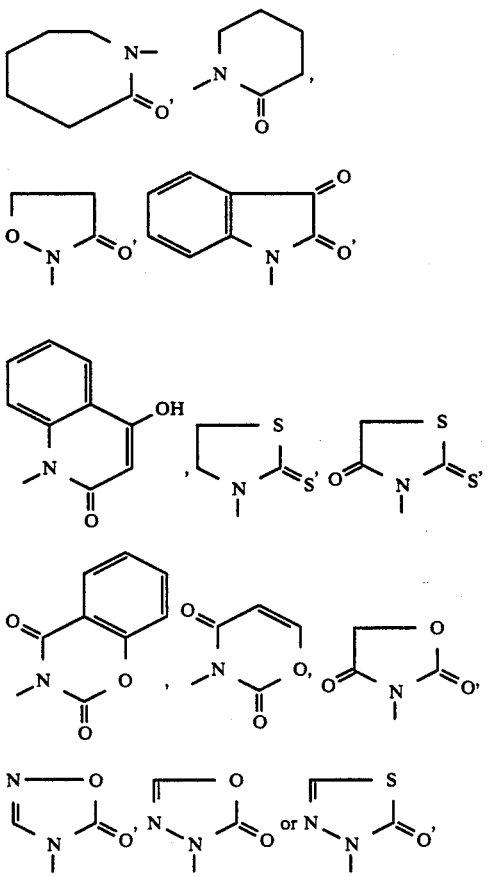

preferably of the formula

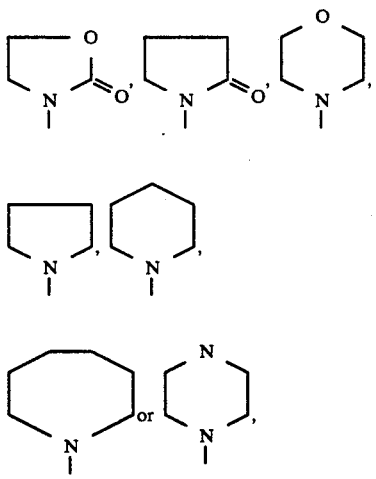

in each case optionally substituted by one to five identical or different substituents from the group comprising methyl, methoxy, methylthio, hydroxyl, mercapto, the oxo or thioxo group, carboxyl, methoxycarbonyl, ethoxycarbonyl, carbamoyl and phenyl;

$R^5$ represents hydrogen, or represents straight-chain or branched alkyl having 1 to 4 carbon atoms which is optionally substituted by one to three identical or different substituents, the following substituents being possible fluorine, chlorine, $-OR^{IV}$, $-SR^{IV}$, $-COOR^{I}$, $-CONR^{II}R^{III}$, CN, $NR^{II}R^{III}$, alkylcarbonyl having 1 to 4 carbon atoms in the straight-chain or branched alkyl part, phenyl and phenoxy, in each case optionally substituted by one to three identical or different substituents from the group comprising halogen and methyl, cyclopropyl, cyclohexyl, cyclopentenyl and cyclohexenyl, in each case optionally substituted by one to three methyl groups, and 3- to 6-membered heterocyclyl having 1 to 3 identical or different hetero atoms, such as nitrogen, oxygen and sulphur atoms, which is optionally substituted by one to three identical or different substituents from the group comprising halogen, methyl and ethyl; $R^5$ furthermore represents allyl or propargyl, optionally substituted by one or two methyl groups, or represents cyclopropyl, cyclohexyl, cyclopentenyl or cyclohexenyl, in each case optionally substituted by one to three methyl groups;

$R^6$ represents hydrogen, or represents straight-chain or branched alkyl having 1 to 4 carbon atoms which is optionally substituted by one or two identical or different substituents, preferred substituents which may be mentioned being: halogen, cyano, $-COOR^{I}$, $-CONR^{II}R^{III}$, $NR^{II}R^{III}$, $-OR^{IV}$, $-S(O)_nR^{IV}$, acyl having 2 to 9 carbon atoms, phenyl which is optionally substituted by one to three identical or different halogen atoms and alkyl groups having 1 to 4 carbon atoms, 5- or 6-membered heterocyclyl having 1 to 3 identical or different hetero atoms, in particular nitrogen, oxygen and sulphur, which is optionally substituted by one to three identical or different halogen atoms and straight-chain or branched alkyl and alkoxy groups having in each case 1 to 4 carbon atoms, and cycloalkyl having 3 to 6 carbon atoms or cycloalkenyl having 5 to 7 carbon atoms, in each case optionally substituted by one to three identical or different straight-chain or branched alkyl groups having 1 to 4 carbon atoms; $R^6$ furthermore particularly preferably represents straight-chain or branched alkenyl or alkynyl having in each case 2 to 6 carbon atoms; or represents cycloalkenyl having 5 to 7 carbon atoms which is optionally substituted by one to three identical or different straight-chain or branched alkyl groups having 1 to 4 carbon atoms, or represents cycloalkyl having 3 to 6 carbon atoms which is optionally substituted by one to three identical or different substituents, preferred substituents which may be mentioned being: halogen, straight-chain or branched alkyl and alkoxy having in each case 1 to 4 carbon atoms, cyano, amino, carbamoyl, in each case straight-chain or branched alkylamino, dialkylamino, alkylcarbamoyl and dialkylcarbamoyl having in each case 1 to 4 carbon atoms in each alkyl part, alkoxycarbonylamino having 1 to 4 carbon atoms in the straight-chain or branched alkoxy part, cycloalkyl and cycloalkylalkyl having in each case 5 or 6 carbon atoms in the cycloalkyl part and 1 to 4 carbon atoms in the straight-chain or branched alkyl part, phenyl which is optionally substituted by one to three identical or different halogen atoms and alkyl groups having 1 to 4 carbon atoms or pyrrolidone; $R^6$ furthermore particularly preferably represents phenyl which is optionally substituted by one to three identical or different substituents from the group comprising halogen, straight-chain or branched alkyl and alkoxy having in each case 1 to 4 carbon atoms and halogenoalkyl and halogenoalkoxy having in each case 1 or 2 carbon atoms and 1 to 5 identical or different halogen atoms, or represents a 5- or 6-membered heterocyclic radical having 1 to 3 identical or different hetero atoms, such as, in particular, nitrogen, oxygen or sulphur, which is optionally substituted by one to three identical or different substituents; substituents which may be mentioned for the heterocyclic radicals are: halogen, mercapto, phenyl and straight-chain or branched alkyl, alkoxy, alkylthio, alkylsulphinyl and alkylsulphonyl having 1 to 4 carbon atoms per alkyl part;

$R^7$ has the meanings of $R^6$ or represents the grouping —$OR^{IV}$, or $R^6$ and $R^7$, together with the nitrogen atom to which they are bonded, represent a mono-, bi- or tricyclic heterocyclic or spiroheterocyclic radical which is optionally substituted by one to five identical or different substituents, heterocyclic radicals which may be mentioned being: oxazolidine, pyrrolidine, imidazolidine, piperidine, piperazine, morpholine, thiomorpholine, 1,3-oxazane and 1,3-diazane; these heterocyclic radicals can in each case be optionally fused with 1 or 2 benzene or cyclohexane rings or optionally bridged with methylene or ethylene.

Substituents which may be mentioned for all the hetero systems are: straight-chain or branched alkyl and cycloalkyl having 3 to 6 carbon atoms, the hydroxyl or the oxo group, straight-chain or branched alkenyl having 2 to 4 carbon atoms, carboxyl, alkoxycarbonyl having 1 to 4 carbon atoms in the straight-chain or branched alkyl part, carbamoyl, alkyl- and dialkylcarbamoyl having in each case 1 to 4 carbon atoms in each alkyl part, and furthermore phenyl and phenylalkyl having 1 to 4 carbon atoms in the straight-chain or branched alkyl part, in each case optionally substituted by one or two identical or different halogen atoms and straight-chain or branched alkyl and alkoxy groups having in each case 1 to 4 carbon atoms, $R^I$ represents hydrogen or straight-chain or branched alkyl having 1 to 4 carbon atoms, $R^{II}$ and $R^{III}$ are identical or different and represent hydrogen, straight-chain or branched alkyl having 1 to 4 carbon atoms or benzyl or phenethyl, in each case optionally substituted by one to three identical or different substituents, substituents on phenyl which may be mentioned in each case being: fluorine, chlorine, methyl, methoxy and trifluoromethyl; $R^{II}$ furthermore represents alkoxycarbonylalkyl having 1 to 4 carbon atoms in the alkoxy part and 1 or 2 carbon atoms in the alkyl part, carbamoylalkyl having 1 or 2 carbon atoms in the alkyl part, alkylcarbamoylalkyl or dialkylcarbamoylalkyl having in each case 1 or 2 carbon atoms in each alkyl part or cycloalkyl having 3 to 6 carbon atoms which is optionally substituted by one to three identical or different substituents from the group comprising methyl and ethyl, $R^{IV}$ represents hydrogen, straight-chain or branched alkyl having 1 to 4 carbon atoms, or benzyl or phenethyl, in each case optionally substituted by one to three identical or different substituents, substituents on phenyl which may be mentioned in each case being: fluorine, chlorine, methyl, methoxy and trifluoromethyl; $R^{IV}$ furthermore represents acyl having 2 to 9 carbon atoms; and $R^V$ represents hydrogen or straight-chain or branched alkyl having 1 to 4 carbon atoms, or represents benzyl or phenethyl, in each case optionally substituted by one to three identical or different substituents, possible substituents on phenyl being the substituents on phenyl mentioned for $R^{II}$.

In addition to the compounds mentioned in the preparation examples, the substances of the formula (I) listed in the following Table 1 may be mentioned as examples of compounds according to the invention:

TABLE 1

$$R^1O-N=C(CN)-C(=O)-NH-CH(R^2)-N(R^3)-A_n-R^4 \quad (I)$$

| $R^1$ | $R^2$ | $-N(R^3)-A_n-R^4$ |
|---|---|---|
| CH₃ | H | $-N(CH_3)-C(=O)-OCH_3$ |
| CH₃ | H | $-N(CH_3)-C(=O)-OC_2H_5$ |
| CH₃ | H | $-N(H)-SO_2-CH_3$ |
| CH₃ | H | $-N(CH_3)-SO_2-CH_3$ |
| CH₃ | H | $-N(CHO)-SO_2-CH_3$ |
| CH₃ | H | $-N(COCH_3)-SO_2-CH_3$ |
| CH₃ | H | saccharin-N-yl (benzisothiazol-3(2H)-one 1,1-dioxide) |
| CH₃ | H | $-N(H)-SO_2-C_6H_5$ |
| CH₃ | H | benzoxazolin-2-one-3-yl |
| CH₃ | H | 3-methyl-5-oxo-4,5-dihydro-pyrazol-1-yl |
| CH₃ | H | 2,5-dioxopyrrolidin-1-yl |
| CH₃ | H | 2-oxo-hexahydroazepin-1-yl |

TABLE 1-continued
$$R^1O-N=\overset{CN}{\underset{O}{C}}-NH-\overset{R^2}{\underset{}{CH}}-\overset{R^3}{\underset{}{N}}-A_n-R^4 \quad (I)$$
| R¹ | R² | —N(R³)—Aₙ—R⁴ |
|---|---|---|
| CH₃ | H | 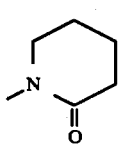 |
| CH₃ | H | 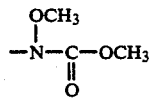 |
| CH₃ | H | 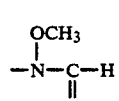 |
| CH₃ | H | 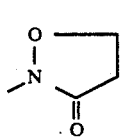 |
| CH₃ | H | 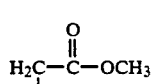 |
| CH₃ | H | 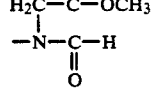 |
| CH₃ | H | 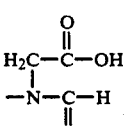 |
| CH₃ | H | 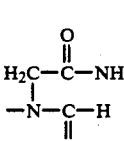 |
| CH₃ | H | 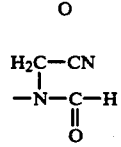 |
| CH₃ | H | 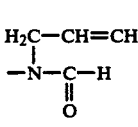 |
| CH₃ | H | 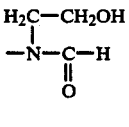 |
| CH₃ | H | 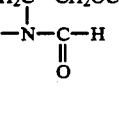 |
| CH₃ | H |  |
| CH₃ | H | 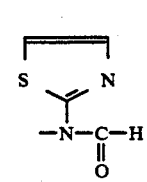 |
| CH₃ | H | 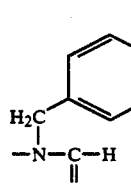 |
| CH₃ | H | 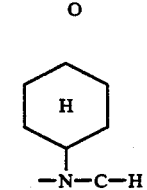 |
| CH₃ | H | 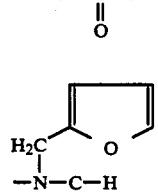 |
| CH₃ | H | 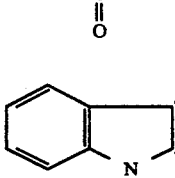 |
| CH₃ | H | 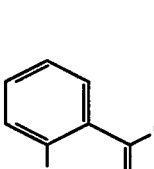 |
| CH₃ | H | 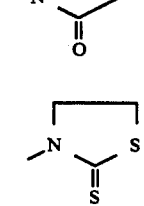 |
| CH₃ | H |  |

TABLE 1-continued $$\underset{R^1O-N=C-C-NH-CH-N-A_n-R^4}{\overset{CN}{\underset{O}{\|}}\overset{R^3}{\underset{R^2}{|}}} \quad (I)$$

| $R^1$ | $R^2$ | $-N(R^3)-A_n-R^4$ |
|---|---|---|
| $CH_3$ | H | cyclopropane with $-C(=O)OCH_3$ and $-N-CHO$ |
| $CH_3$ | H | $-N(CHO)-C(=O)OCH_3$ |
| $CH_3$ | H | $-N(COCH_3)-C(=O)OCH_3$ |
| $CH_3$ | H | $-N(CO-OCH_3)-C(=O)OCH_3$ |
| $CH_3$ | H | N-methyl-5-oxopyrrolidine-2-carboxylic acid |
| $CH_3$ | H | 1-methylisatin (1-methyl-2,3-dioxoindoline) |
| $CH_3$ | H | N-methylphthalimide |
| $CH_3$ | H | 3-methyl-2-thioxothiazolidine |
| $CH_3$ | H | N-methyl-4H-benzo[d][1,3]oxazine-2,4-dione |
| $CH_3$ | H | ethyl ester of 3-methyl-2,4-dioxo-2H,4H-[1,3]oxazine |
| $CH_3$ | H | $-N(COCH_2Cl)-C(=O)OCH_3$ |
| $CH_3$ | H | 3,4,4-trimethyl-1,3-oxazolidine-2,5-dione-like |
| $CH_3$ | H | 3,4-dimethyl-1,2,4-oxadiazol-5(4H)-one |
| $CH_3$ | H | 3-methyl-4-phenyl-1,2,4-oxadiazol-5(4H)-one |
| $CH_3$ | H | 2-methyl-5-phenyl-2,3-dihydro-1,3,4-oxadiazol-3-one |
| $CH_3$ | $CH_3$ | $-N(CH_3)-CHO$ |
| $-CH_2-C_6H_5$ | H | $-N(CHO)-C(=O)OCH_3$ |
| $-CH_2-C_6H_5$ | H | $-N(CHO)-SO_2CH_3$ |
| $CH_3$ | $-C_6H_5$ | $-N(H)-SO_2CH_3$ |

TABLE 1-continued $$R^1O-N=\overset{CN}{\underset{\underset{O}{\overset{\|}{C}}}{C}}-NH-\overset{R^3}{\underset{R^2}{CH}}-\overset{R^3}{\underset{}{N}}-A_n-R^4 \quad (I)$$

| $R^1$ | $R^2$ | $-\overset{R^3}{\underset{}{N}}-A_n-R^4$ |
|---|---|---|
| $-CH_2-C\equiv N$ | H | 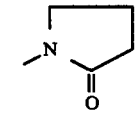 |
| 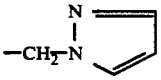 | H | 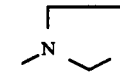 |
| $CH_3$ | 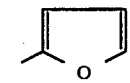 | 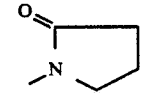 |
| $-CH_2-CH=CH_2$ | H | 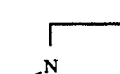 |
| $CH_3$ | H | $\underset{\underset{CH_3}{\|}}{-N}-CH_2CH_2CN$ |
| $CH_3$ | H | 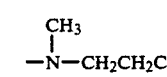 |
| $CH_3$ | H | 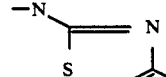 |
| $CH_3$ | H | 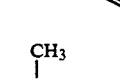 |

If, for example, (E)-2-cyano-2-methoximino-acetyl chloride and N-aminomethylphthalimide hydrochloride are used as starting substances, triethylamine is used as the base and 4-dimethylaminopyridine is used as the catalyst, the course of the reaction in process (a) according to the invention can be represented by the following equation:

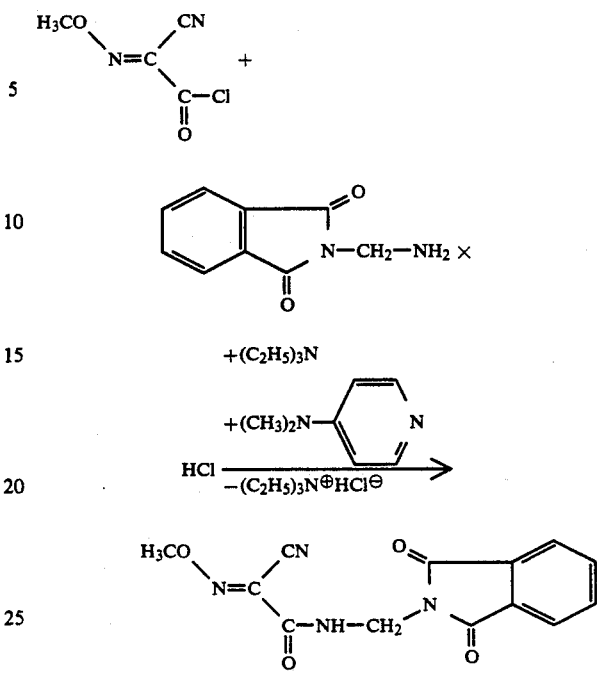

If, for example, (E)-2-cyano-2-methoximinoacetamide and N-hydroxymethyl-2-pyrrolidone are used as starting substances and sulphuric acid is used as the acid, the course of the reaction in process (b) according to the invention can be represented by the following equation:

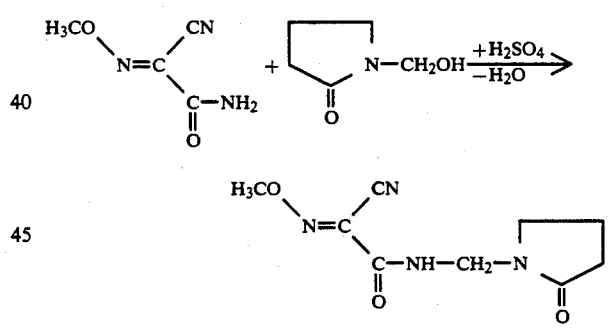

If, for example, (E)-2-cyano-2-methoximinoacetamide and N-chloromethyl-N-methoxycarbonylmethylamine are used as starting substances and triethylamine is used as the base, the course of the reaction in process (c) according to the invention can be represented by the following equation:

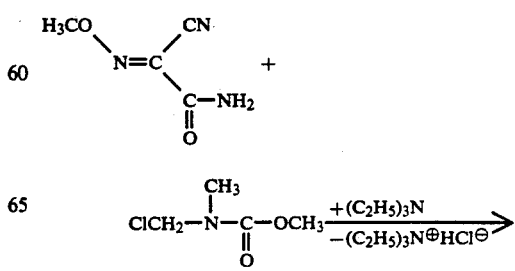

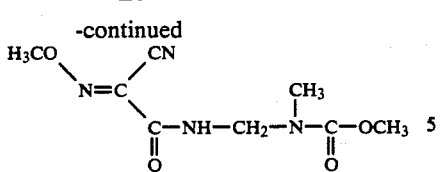

If, for example, (E)-2-cyano-2-methoximinoacetamide, dimethylamine and formaldehyde are used as starting substances, the course of the reaction in process (d) according to the invention can be represented by the following equation:

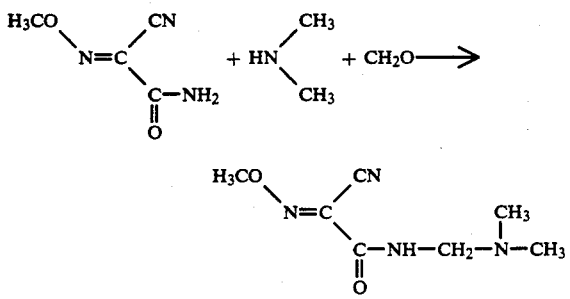

If, for example, (E)-N-aminomethyl-2-cyano-2-methoximinoacetamide hydrochloride is used as the starting substance, phenyl chloroformate is used as the acylating reagent, triethylamine is used as the base and 4-dimethylaminopyridine is used as the catalyst, the course of the reaction in process (e) according to the invention can be represented by the following equation:

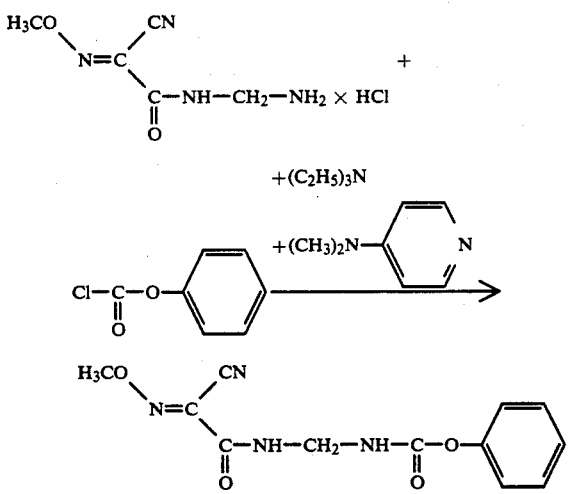

Formula (II) provides a general definition of the 2-cyano-2-oximinocarbonyl compounds to be used as starting substances in process (a) according to the invention for the preparation of compounds of the formula (I).

In formula (II), $R^1$ preferably or in particular has those meanings which have already been mentioned above as preferred or as particularly preferred for $R^1$ in connection with the description of the compounds of the formula (I) according to the invention.

The 2-cyano-2-oximinocarbonyl compounds of the formula (II) are known and/or can be prepared by processes which are known per se (compare, for example, DE-OS (German Published Specification) 3,728,277/European Patent 304,758).

Formula (III) provides a general definition of the amino compounds furthermore to be used as starting substances in process (a) according to the invention for the preparation of compounds of the formula (I).

In formula (III), $R^2$, $R^3$, $R^4$, A and n preferably or in particular have those meanings which have already been mentioned above as preferred or as particularly preferred for $R^2$, $R^3$, $R^4$, A and n in connection with the description of the compounds of the formula (I) according to the invention.

HY preferably represents the equivalent of a mineral acid, such as, for example, hydrochloric acid, or a carboxylic acid, such as, for example, oxalic acid.

The amino compounds of the formula (III) are known in some cases (compare, for example, J. Heterocycl. Chem. 16, 339 (1979), or they can be prepared by processes which are known per se, by reacting halogen compounds of the formula (VI)

in which $R^2$, $R^3$, $R^4$, A and n have the abovementioned meanings and

X represents chlorine or bromine, with urotropine, if appropriate in the presence of a diluent, such as, for example, chloroform, at temperatures between 0° C. and 100° C., and hydrolyzing the resulting intermediate product of the formula (X)

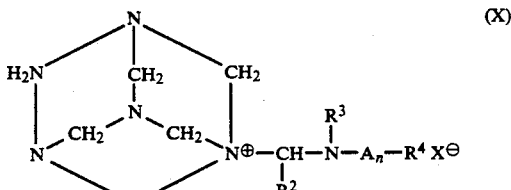

in which $R^2$, $R^3$, $R^4$, A and n have the abovementioned meanings and

X represents chlorine or bromine, with a mineral acid, such as, for example, hydrochloric acid.

The halogen compounds of the formula (VI)

are known in some cases (compare, for example, DE-OS (German Published Specification) 2,119,518), or they can be prepared, for example, by converting compounds of the formula (XI)

in which $R^3$, $R^4$, A and n have the abovementioned meanings, into the halogen compounds of the formula (VI) by reaction with an aldehyde of the formula (XII)

$$R^2CHO \qquad (XII)$$

in which $R^2$ has the abovementioned meaning, and a halogenating reagent, such as, for example, thionyl chloride, if appropriate in the presence of a diluent, such as, for example, toluene or chloroform, at temperatures from 0° C. to 150° C.

The compounds of the formula (XI) are known and/or can be prepared by processes which are known per se (compare CA 107, 156950y). The aldehydes of the formula (XII) are generally known synthesis chemicals.

Formula (IV) provides a general definition of the 2-cyano-2-oximinoacetamides to be used as starting substances in processes (b), (c) and (d) according to the invention for the preparation of compounds of the formula (I).

In formula (IV), $R^1$ preferably or in particular has those meanings which have already been mentioned above as preferred or as particularly preferred for $R^1$ in connection with the description of the compounds of the formula (I) according to the invention.

The 2-cyano-2-oximinoacetamides of the formula (IV) are known and/or can be prepared by processes analogous to known processes (compare, for example, Chem. Ber. 54, 1342 (1921); DE-OS (German Published Specification) 2,623,847; DE-OS (German Published Specification) 2,657,145 and DE-OS (German Published Specification) 3,702,283).

Formula (V) provides a general definition of the compounds to be used as starting substances in process (b) according to the invention for the preparation of compounds of the formula (I).

In formula (V), $R^2$, $R^3$, $R^4$, A and n preferably or in particular have those meanings which have already been mentioned above as preferred or as particularly preferred for $R^2$, $R^3$, $R^4$, A and n in connection with the description of the compounds of the formula (I) according to the invention. $R^8$ preferably represents hydrogen, methyl or acetyl.

The compounds of the formula (V) are known (compare, for example, Beilstein 21 4th supplement; and Tetrahedron Lett. 27, 3525 (1986)) and/or can be prepared by known processes, for example by reacting compounds of the formula (XI)

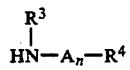
(XI)

in which $R^3$, $R^4$, A and n have the abovementioned meanings, with aldehydes of the formula (XII), if appropriate in the presence of a diluent, such as ethanol or ethyl acetate, at temperatures from 0° C. to 100° C., to give the hydroxy compounds of the formula (Va)

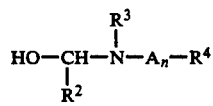
(Va)

in which $R^2$, $R^3$, $R^4$, A and n have the abovementioned meanings, and in a subsequent reaction forming a derivative of the hydroxyl group by acetylation with acetic anhydride or acetyl chloride or by esterification with methanol in the presence of sulphuric acid or hydrogen chloride.

Formula (VI) provides a general definition of the halogen compounds furthermore to be used as starting substances in process (c) according to the invention for the preparation of compounds of the formula (I).

In formula (VI), $R^2$, $R^3$, $R^4$, A and n preferably or in particular have those meanings which have already been mentioned above as preferred or as particularly preferred for $R^2$, $R^3$, $R^4$, A and n in connection with the description of the compounds of the formula (I) according to the invention. X preferably represents chlorine or bromine.

The halogen compounds of the formula (VI) are known and/or can be prepared by known processes (compare process (a)).

Formula (VII) provides a general definition of the amines furthermore to be used as starting substances in process (d) according to the invention for the preparation of compounds of the formula (I).

In formula (VII), $R^3$ and $R^4$ preferably or in particular have those meanings which have already been mentioned above as preferred or as particularly preferred for $R^3$ and $R^4$ in connection with the description of the compounds of the formula (I) according to the invention.

Amines of the formula (VII) are generally known compounds of organic chemistry.

Formula (VIII) provides a general definition of the N-(2-cyano-2-oximino-acetyl)-aminals to be used as starting substances in process (e) according to the invention for the preparation of compounds of the formula (I).

In formula (VIII), $R^1$ and $R^2$ preferably or in particular have those meanings which have already been mentioned above as preferred or as particularly preferred for $R^1$ and $R^2$ in connection with the description of the compounds of the formula (I) according to the invention.

HY represents the equivalent of a mineral acid, such as, for example, hydrochloric acid, or a carboxylic acid, such as, for example, oxalic acid.

The N-(2-cyano-2-oximino-acetyl)-aminals of the formula (VIII) are known and/or can be prepared by known processes (compare DE-OS (German Published Specification) 3,728,277/European Patent 304,758).

Formula (IX) provides a general definition of the acylating reagents to be used as starting substances in process (e) according to the invention for the preparation of compounds of the formula (I).

In formula (IX), $R^4$ and A preferably or in particular have those meanings which have already been mentioned above as preferred or as particularly preferred for $R^4$ and A in connection with the description of the compounds of the formula (I) according to the invention and Q preferably represents a leaving group.

Leaving groups include, preferably, chlorine, bromine, alkoxy and alkylthio having in each case 1 to 4 carbon atoms, carboxymethoxy, carboxymethylthio and the groupings $-O-CO-R^4$, $-O-CO-OR^5$, $-OR^5$ and $SR^5$. In these groupings, $R^4$ and $R^5$ preferably have the meanings which have already been mentioned as preferred for these substituents in connection with the description of the substances of the formula (I) according to the invention.

The acylating reagents of the formula (IX), that is to say carboxylic acid halides, carboxylic acid anhydrides, halogenoformic acid esters and thiolesters, trithiocarbonates, pyrocarbonates, carbamic acid halides, carbamates, thiol-carbamates, dithiocarbamates, isocyanates or isothiocyanates, are generally known compounds of organic chemistry or are obtainable by generally customary methods.

Processes (a) and (e) according to the invention are preferably carried out using diluents.

Possible diluents here are inert organic solvents. These include, preferably, aromatic hydrocarbons, such as toluene; halogenated hydrocarbons, such as methylene chloride or chloroform; ethers, such as tetrahydrofuran or 1,2-dimethoxyethane; esters, such as ethyl acetate; nitriles, such as acetonitrile; ketones, such as acetone; tertiary amines, such as pyridine; and amides, such as dimethylformamide.

Processes (a) and (e) according to the invention are carried out in the presence of a base. The customary organic and inorganic bases are suitable here. Bases which may be mentioned as preferred are tertiary amines, such as triethylamine or pyridine; alcoholates, such as sodium methylate, and alkali metal carbonates, such as potassium carbonate.

If appropriate, processes (a) and (e) according to the invention are carried out in the presence of a catalyst. Examples of catalysts which may be mentioned are tertiary amines, such as 4-dimethylaminopyridine, 1,8-diazabicyclo[5,4,0]-undec-7-ene (DBU) or 1,4-diazabicyclo[2,2,2]-octane (DBCO); and furthermore imidazole and dimethylformamide.

The reaction temperatures can be varied within a substantial range in carrying out processes (a) and (e) according to the invention. The reaction is in general carried out at temperatures from $-20°$ C. to $120°$ C., preferably from $0°$ C. to $40°$ C.

In carrying out process (a) according to the invention, equimolar amounts are preferably used. However, it is also possible for one of the two components employed and the base to be used in a relatively large excess.

In carrying out process (e) according to the invention, equimolar amounts are preferably used, but the N-(2-cyano-2-oximino-acetyl)-aminals of the formula (VIII) or the acylating reagent of the formula (IX) and the base can also be employed in excess. The reaction is carried out and the products are worked up by generally customary methods in processes (a) and (e).

Process (b) according to the invention is preferably carried out using diluents. Possible diluents are: aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and dichlorobenzene, ethers, such as diethyl ether, dibutyl ether, glycol dimethyl ether, diglycol dimethyl ether, tetrahydrofuran and dioxane, esters, such as methyl and ethyl acetate, nitriles, such as, for example, acetonitrile and propionitrile, amides, such as, for example, dimethylformamide, dimethylacetamide and N-methyl-pyrrolidone, and dimethyl sulphoxide, carboxylic acids, such as acetic acid, alcohols, such as methanol, ethanol or isopropanol, and water.

Process (b) according to the invention is carried out in the presence of reaction auxiliaries. Examples of possible reaction auxiliaries are mineral acids, such as sulphuric acid or hydrochloric acid, or strongly acid ion exchangers, such as Levatit S100 or SPC 108.

The reaction temperatures can be varied within a substantial range in process (b) according to the invention. The reaction is in general carried out at temperatures from $0°$ C. to $+150°$ C., preferably at temperatures from $+40°$ C. to $+100°$ C.

In carrying out process (b) according to the invention, equimolar amounts are preferably used, but it is also possible for one of the two components employed and the mineral acid to be used in a relatively large excess. If an ion exchanger is used as an auxiliary, this is employed in a catalytic amount.

The reaction is carried out and the products are worked up by generally customary methods.

Process (c) according to the invention is preferably carried out using diluents. Possible diluents are: ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl and ethyl acetate, and nitriles, such as, for example, acetonitrile and propionitrile, acetonitrile or ethyl acetate preferably being used.

Process (c) according to the invention is carried out in the presence of a base. Possible bases here are the customary organic and inorganic bases. Bases which may be mentioned as preferred are tertiary amines, such as triethylamine or pyridine; alcoholates, such as sodium methylate, and alkali metal carbonates, such as potassium carbonate.

The reaction temperatures can be varied within a substantial range in process (c) according to the invention. The reaction is in general carried out at temperatures between $0°$ C. to $+160°$ C., preferably at temperatures from $+40°$ C. to $+100°$ C.

Equimolar amounts are preferably used for carrying out process (c) according to the invention, but it is also possible for one of the two components employed and the base to be used in a relatively large excess.

The reaction is carried out and the products are worked up by generally customary methods.

Process (d) according to the invention is preferably carried out using diluents. Possible diluents are: water, alcohols, such as methanol, ethanol and t-butanol, water-miscible ethers, such as glycol dimethyl ether, diglycol dimethyl ether, tetrahydrofuran and dioxane, and nitriles, such as, for example, acetonitrile and propionitrile, mixtures of water and alcohol preferably being used.

The reaction temperatures can be varied within a substantial range in process (d) according to the invention. The reaction is in general carried out at temperatures from $-20°$ C. to $+120°$ C., preferably at temperatures from $0°$ C. to $+100°$ C.

In carrying out process (d) according to the invention, equimolar amounts are preferably used, but it is also possible for one of the three components used to be employed in a relatively large excess. The reaction is carried out and the products are worked up by generally customary methods, and the reaction products are isolated, if appropriate, by chromatography.

The active compounds according to the invention exhibit a potent microbicidal action and can be employed in practice for combating undesirable microorganisms. The active compounds are suitable for use as agents for combating pests, in particular as fungicides.

Fungicidal agents in plant protection are employed, for example, for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*; Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P.brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: *Helminthosporium*);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea*; Septoria species, such as, for example, *Septoria nodorum*; Leptosphaeria species, such as, for example, *Leptosphaeria nodorum;*

Cercospora species, such as, for example, *Cercospora canescens;*

Pseudocercosporella species, such as, for example, *Pseudocerco sporella herpotrichoides.*

The good toleration, by plants, of the active compounds, at the concentrations required for combating plant diseases, permits treatment of above-ground parts of plants, of vegetative propagation stock and seeds, and of the soil.

In agents for combating pests, the active compounds according to the invention can be employed with particularly good success for combating Phytophthora species, such as, for example, *Phytophthora infestans*, on tomatoes; and also for combating Plasmopara species, such as, for example, *Plasmopara viticola*, on vines.

Some of the active compounds according to the invention moreover exhibit a good fungicidal action against Pyricularia on rice.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformanride and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Preparation Examples

Example 1

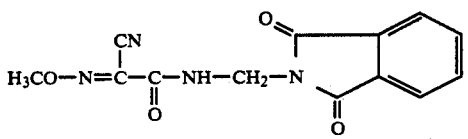

Process (a)

12.0 g (80 mmol) of (E)-2-cyano-2-methoximinoacetyl chloride and then a solution of 16.0 g (158 mmol) of triethylamine and 1.0 g (8 mmol) of 4-dimethylaminopyridine in 20 ml of dry dimethylformamide are added dropwise to a suspension of 24.0 g (80 mmol) of N-aminomethylphthalimide hydrochloride in 80 ml of dry dimethylformamide at a temperature of 0° C. The mixture is stirred at 0° C. for 1 hour and at room temperature for 15 hours, the precipitate formed is filtered off with suction and washed with dimethylformamide and the solvent is removed under reduced pressure. The residue is taken up in 200 ml of ethyl acetate and 70 ml of water and the organic phase is separated off, washed with 70 ml each of 1N hydrochloric acid, saturated sodium bicarbonate solution and water and dried over sodium sulphate.

Chromatography on silica gel 60 with methylene chloride as the mobile phase gives 8.2 g (30% of theory) of (E)-2-cyano-2-methoximino-N-(phthalimidomethyl)acetamide of melting point 150°-152° C.

Example 2

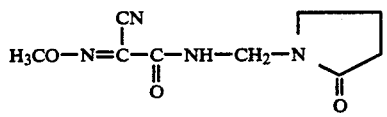

Process (b)

6.55 g (0 05 mol) of (E)-2-cyano-2-methoximinoacetamide and 5.75 g (0.05 mol) of N-hydroxymethyl-2-pyrrolidone are suspended in 75 ml of concentrated acetic acid, and 11.25 g (0.11 mol) of concentrated sulphuric acid are added dropwise at a temperature of 20°-25° C.

(while cooling). The mixture is then stirred at room temperature for a further 28 hours.

100 ml of ice-water are carefully added to the reaction mixture and the mixture is extracted 5 times with 100 ml of methylene chloride each time. The combined extracts are dried over sodium sulphate. After removal of the solvent by distillation, the residue is recrystallized from water.

7.95 g (70% of theory) of N-[(E)-2-cyano-2-methoximinoacetamidomethyl]-2-pyrrolidone of melting point 160°-162° C. are obtained.

Example 3

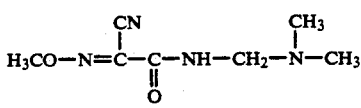

Process (d)

A mixture of 38.1 g (0.3 mol) of (E)-2-cyano-2-methoximinoacetamide, 300 ml of tert.-butanol, 79.5 g (0.6 mol) of dimethylamine (in the form of a 34% strength aqueous solution) and 48.6 g (0.6 mol) of formaldehyde (in the form of a 37% strength aqueous solution) is heated at room temperature for 30 minutes and under reflux for 15 minutes. The solvents are removed by distillation and the residue is recrystallized from petroleum ether/ether (1:7).

53.8 g (97% of theory) of (E)-2-cyano-N-dimethylaminomethyl-2-methoximinoacetamide of melting point 50°-52° C. are obtained.

The compounds of the formula (I)

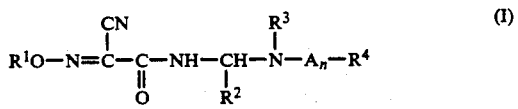

shown in the following Table 2 can be prepared analogously to the examples and in accordance with the general information on processes (a), (b), (c), (d) and (e).

TABLE 2

| Example No. | $R^1$ | $R^2$ | $-N-A_n-R^4$ with $R^3$ | Melting point |
|---|---|---|---|---|
| 4 | CH₃ | H | morpholino | 134-135° C. |
| 5 | CH₃ | H | pyrrolidino | 68-70° C. |
| 6 | CH₃ | H | piperidino | 116-117° C. |
| 7 | CH₃ | H | -N(C₂H₅)₂ | oil |

TABLE 2-continued

| Example No. | R¹ | R² | $-\overset{R^3}{\underset{|}{N}}-A_n-R^4$ | Melting point |
|---|---|---|---|---|
| 8 | CH₃ | H | —N(CH₂—CH=CH₂)(CH₂—CH=CH₂) (diallylamino) | 50–51° C. |
| 9 | CH₃ | H | 2,6-dimethylmorpholin-4-yl | 102–103° C. |
| 10 | CH₃ | H | hexamethyleneimin-1-yl | 99–100° C. |
| 11 | CH₃ | H | 4-methylpiperazin-1-yl | 99–100° C. |
| 12 | CH₃ | H | —N(CH₃)—cyclohexyl | oil |
| 13 | CH₃ | H | —N(CH₃)—CH₂—C₆H₅ | 62–63° C. |
| 14 | CH₃ | H | —N(CH₃)—CH₂-(furan-2-yl) | oil |
| 15 | CH₃ | H | —N(CH₃)—CH₂—CH(OCH₃)—OCH₃ | oil |
| 16 | CH₃ | H | morpholin-3-on-4-yl | 125–126° C. |
| 17 | CH₃ | H | —N(H)—C(=O)—C(CN)=N—OCH₃ | 142–144° C. |
| 18 | CH₃ | H | —N(CH₃)—C(=O)—OCH₃ | 131–132° C. |
| 19 | CH₃ | H | —N(CH₃)—C(=O)—H | 117–119° C. |
| 20 | CH₃ | H | —N(C₂H₅)—C(=O)—OCH₃ | 63–64° C. |

Use Examples

The compound shown below is employed as comparison substance in the use examples which follow:

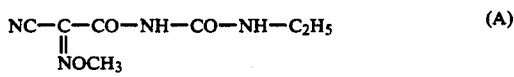
  (A)

2-cyano-N-[(ethylamino)carbonyl]-2-(methoximino)acetamide (known from DE-OS (German Published Specification) 2,312,956)

Example A

Phytophthora Test (tomato)/curative

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous spore suspension of Phytophthora infestans. The plants remain in an incubation cabin at 20° C. and 100% relative atmospheric humidity for 7 hours. After a short drying-off time, the plants are sprayed with the preparation of active compound until dripping wet.

The plants are placed in an incubation cabin at 100% relative atmospheric humidity at about 20° C.

Evaluation is carried out 3 days after the inoculation.

In this test, a good fungicidal activity is shown, for example, by the compounds according to the following preparation examples: 10, 11, 12 and 13.

Example B

Plasmopara test (vines)/protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Plasmopara viticola and then remain in a humidity chamber at 20° to 22° C. and 100% relative atmospheric humidity for 1 day. The plants are then placed in a greenhouse at 22° C. and about 80% atmospheric humidity for 5 days. The plants are then moistened and placed in a humidity chamber for 1 day.

Evaluation is carried out 7 days after the inoculation.

In this test, a clearly superior activity compared with the prior art is shown, for example, by the compounds according to Preparation Examples (1) and (2).

It is understood that the specification and examples are illustrative but not limitative of the present invention and that other embodiments within the spirit and scope of the invention will suggest themselves to those skilled in the art.

We claim:

1. An aminal of the formula

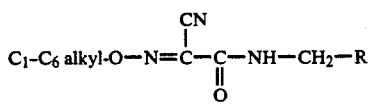

on which R represents a heterocyclyl of the formula

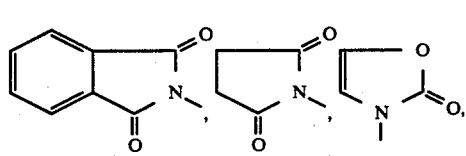

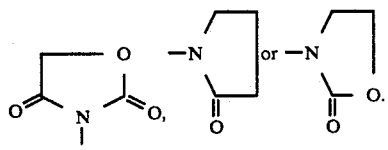

2. A compound according to claim 1, wherein such compound is (E)-2-cyano-2-methoximino-N-(phthalimidomethyl)acetamide of the formula

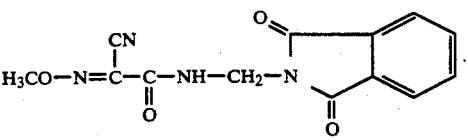

3. A compound according to claim 1, wherein such compound is N-[(E)-2-cyano-2-methoximinoacetamidomethyl]-2-pyrrolidone of the formula

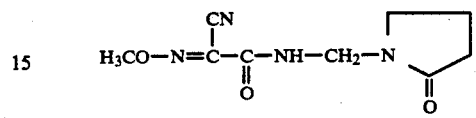

4. A fungicidal composition comprising a fungicidally effective amount of a compound according to claim 1 and a diluent.

5. A method of combatting fungi which comprises applying to such fungi or to a fungus habitat a fungicidally effective amount of a compound according to claim 1.

6. The method according to claim 5, wherein such compound is
(E)-2-cyano-2-methoximino-N-(phthalimidomethyl-)acetamide,
N-[(E)-2-cyano-2-methoximinoacetamidomethyl]-2-pyrrolidone.

* * * * *